(12) United States Patent
Zhao et al.

(10) Patent No.: US 10,258,548 B2
(45) Date of Patent: Apr. 16, 2019

(54) HAIR CARE CONDITIONING COMPOSITION

(71) Applicant: The Procter & Gamble Company, Cincinnati, OH (US)

(72) Inventors: Jean Jianqun Zhao, Cincinnati, OH (US); Robert Wayne Glenn, Jr., Liberty Township, OH (US); Sarah Elizabeth Mullen, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 182 days.

(21) Appl. No.: 15/135,712

(22) Filed: Apr. 22, 2016

(65) Prior Publication Data

US 2016/0310371 A1    Oct. 27, 2016

Related U.S. Application Data

(60) Provisional application No. 62/151,602, filed on Apr. 23, 2015.

(51) Int. Cl.

| | | |
|---|---|---|
| A61K 8/04 | (2006.01) | |
| A61Q 5/12 | (2006.01) | |
| A61K 8/06 | (2006.01) | |
| A61K 8/31 | (2006.01) | |
| A61K 8/34 | (2006.01) | |
| A61K 8/41 | (2006.01) | |
| A61K 8/73 | (2006.01) | |
| A61K 8/81 | (2006.01) | |
| A61K 8/898 | (2006.01) | |
| A61Q 5/00 | (2006.01) | |

(52) U.S. Cl.
CPC ............ *A61K 8/046* (2013.01); *A61K 8/068* (2013.01); *A61K 8/315* (2013.01); *A61K 8/342* (2013.01); *A61K 8/345* (2013.01); *A61K 8/416* (2013.01); *A61K 8/731* (2013.01); *A61K 8/737* (2013.01); *A61K 8/8176* (2013.01); *A61K 8/898* (2013.01); *A61Q 5/006* (2013.01); *A61Q 5/12* (2013.01); *A61K 2800/21* (2013.01); *A61K 2800/30* (2013.01); *A61K 2800/48* (2013.01); *A61K 2800/592* (2013.01); *A61K 2800/594* (2013.01)

(58) Field of Classification Search
None
See application file for complete search history.

(56) References Cited

U.S. PATENT DOCUMENTS

| | | |
|---|---|---|
| 3,236,733 A | 2/1966 | Karsten et al. |
| 3,938,708 A | 2/1976 | Burger |
| 4,607,756 A | 8/1986 | Courtman |
| 4,610,874 A * | 9/1986 | Matravers ............... A61K 8/63 424/70.13 |
| 4,880,618 A | 11/1989 | Grollier et al. |
| 5,012,978 A | 5/1991 | Bolduc |
| 5,077,040 A | 12/1991 | Bergmann et al. |
| 5,635,469 A | 6/1997 | Fowler et al. |
| 5,674,478 A | 10/1997 | Dodd et al. |
| 5,985,295 A | 11/1999 | Peffly |
| 6,039,036 A | 3/2000 | Restle et al. |
| 6,589,509 B2 | 7/2003 | Keller et al. |
| 6,604,693 B2 | 8/2003 | Santagiuliana |
| 6,605,577 B1 | 8/2003 | Harrison et al. |
| 6,642,194 B2 | 11/2003 | Harrison et al. |
| 6,656,458 B1 | 12/2003 | Philippe et al. |
| 6,927,196 B2 | 8/2005 | Snyder et al. |
| 7,001,594 B1 | 2/2006 | Peffly et al. |
| 7,217,777 B2 | 5/2007 | Lange et al. |
| 7,316,815 B2 | 1/2008 | Philippe et al. |
| RE40,534 E | 10/2008 | Harrison et al. |
| 7,455,195 B2 | 11/2008 | Mekata |
| 7,462,585 B2 | 12/2008 | Uehara |
| 7,470,651 B2 | 12/2008 | Uehara et al. |
| 7,504,093 B2 | 3/2009 | Bracken et al. |
| 7,759,378 B2 | 7/2010 | Philippe et al. |
| 8,017,106 B2 | 9/2011 | Keller et al. |
| 8,263,053 B2 | 9/2012 | Duvel et al. |
| 8,475,777 B2 | 7/2013 | Rautschek |
| 8,476,472 B2 | 7/2013 | Hojo et al. |
| 8,642,021 B2 | 2/2014 | Brautigam et al. |
| 8,697,040 B2 | 4/2014 | Duvel et al. |

(Continued)

FOREIGN PATENT DOCUMENTS

| | | |
|---|---|---|
| DE | 10304721 B4 | 3/2007 |
| EP | 978271 A1 | 2/2000 |

(Continued)

OTHER PUBLICATIONS

U.S. Appl. No. 15/380,194, filed Dec. 15, 2016, Glenn, Jr. et al.
U.S. Appl. No. 15/380,218, filed Dec. 15, 2016, Glenn, Jr. et al.
U.S. Appl. No. 15/380,261, filed Dec. 15, 2016, Glenn, Jr. et al.
U.S. Appl. No. 15/380,293, filed Dec. 15, 2016, Glenn, Jr. et al.

(Continued)

*Primary Examiner* — Nannette Holloman
(74) *Attorney, Agent, or Firm* — Angela K. Haughey

(57) ABSTRACT

The hair care composition includes a cationic surfactant, a silicone, and an aqueous carrier, wherein the silicone to high melting point fatty compounds ratio is about 100:0. Additionally, the hair care composition has a liquid phase viscosity of from about 1 centipoise to about 500 centipoise. The hair care composition can be dispensed as a dosage of foam; applying the foam to the hair; and rinsing the foam from the hair. The foam has a density of from about 0.025 g/cm³ to about 0.15 g/cm³ when dispensed from the aerosol foam dispenser.

26 Claims, No Drawings

(56) References Cited

U.S. PATENT DOCUMENTS

| | | |
|---|---|---|
| 8,956,597 B2 | 2/2015 | Gesztesi et al. |
| 8,999,306 B2 | 4/2015 | Duvel et al. |
| 9,255,184 B2 | 2/2016 | Paul |
| 9,308,398 B2 | 4/2016 | Hutton et al. |
| 9,358,186 B2 | 6/2016 | Chandra et al. |
| 9,539,199 B2 | 1/2017 | Beer et al. |
| 9,539,208 B2 | 1/2017 | Tamarkin et al. |
| 9,540,489 B2 | 1/2017 | Panandiker et al. |
| 9,828,170 B2 | 11/2017 | Nomura et al. |
| 9,993,419 B2 | 6/2018 | Glenn, Jr. et al. |
| 2001/0008630 A1 | 7/2001 | Pyles et al. |
| 2001/0025857 A1 | 10/2001 | Baudin |
| 2002/0031532 A1 | 3/2002 | Uchiyama |
| 2002/0143063 A1 | 10/2002 | Alvarado |
| 2002/0197213 A1 | 12/2002 | Schmenger et al. |
| 2003/0152542 A1 | 8/2003 | Decoster et al. |
| 2003/0228272 A1 | 12/2003 | Amjad et al. |
| 2004/0018164 A1 | 1/2004 | Zofchak et al. |
| 2004/0076595 A1 | 4/2004 | Khan |
| 2004/0229763 A1 | 11/2004 | Hutton, III et al. |
| 2004/0247550 A1 | 12/2004 | Asari et al. |
| 2005/0002892 A1 | 1/2005 | Khan et al. |
| 2005/0136011 A1 | 6/2005 | Nekludoff et al. |
| 2005/0152863 A1* | 7/2005 | Brautigam ............. A61K 8/986 424/70.1 |
| 2005/0196372 A1 | 9/2005 | Cajan |
| 2005/0196376 A1 | 9/2005 | Loomis |
| 2005/0197421 A1 | 9/2005 | Loomis |
| 2005/0222001 A1 | 10/2005 | Baumeister et al. |
| 2005/0274737 A1 | 12/2005 | Krause et al. |
| 2006/0034792 A1 | 2/2006 | Lazzeri et al. |
| 2006/0054634 A1 | 3/2006 | Mekata |
| 2006/0083704 A1 | 4/2006 | Torgerson |
| 2006/0275245 A1 | 12/2006 | Decoster et al. |
| 2006/0292104 A1 | 12/2006 | Guskey et al. |
| 2006/0293197 A1 | 12/2006 | Uehara et al. |
| 2007/0179207 A1 | 8/2007 | Fernandez de Castro et al. |
| 2007/0286837 A1 | 12/2007 | Torgerson |
| 2008/0066773 A1 | 3/2008 | Anderson et al. |
| 2008/0138296 A1 | 6/2008 | Tamarkin et al. |
| 2008/0292560 A1 | 11/2008 | Tamarkin et al. |
| 2008/0292574 A1 | 11/2008 | Uehara |
| 2009/0041706 A1 | 2/2009 | Molenda et al. |
| 2009/0155383 A1 | 6/2009 | Kitko et al. |
| 2009/0232759 A1* | 9/2009 | Bell ..................... A61K 8/44 424/70.1 |
| 2010/0092405 A1 | 4/2010 | Philippe et al. |
| 2010/0143280 A1 | 6/2010 | Yokogi et al. |
| 2010/0143281 A1 | 6/2010 | Okada et al. |
| 2010/0143352 A1 | 6/2010 | Yokogi et al. |
| 2010/0143425 A1 | 6/2010 | Okada et al. |
| 2010/0178265 A1 | 7/2010 | Molenda et al. |
| 2011/0135588 A1 | 6/2011 | Uehara et al. |
| 2011/0226273 A1 | 9/2011 | Deardorff et al. |
| 2011/0280110 A1 | 11/2011 | Chen |
| 2011/0318295 A1 | 12/2011 | Shimizu |
| 2012/0020908 A1 | 1/2012 | Paul |
| 2012/0034173 A1 | 2/2012 | Batt et al. |
| 2012/0043352 A1 | 2/2012 | Rasmussen et al. |
| 2012/0114819 A1 | 5/2012 | Ragnarsson |
| 2012/0171147 A1 | 7/2012 | Rautschek |
| 2012/0288465 A1 | 11/2012 | Loechel |
| 2013/0075430 A1 | 3/2013 | Ragnarsson |
| 2013/0202666 A1 | 8/2013 | Petkov et al. |
| 2013/0280192 A1 | 10/2013 | Carter et al. |
| 2013/0284196 A1 | 10/2013 | Murdock et al. |
| 2014/0105943 A1 | 4/2014 | Pistoria et al. |
| 2014/0107224 A1 | 4/2014 | Osman et al. |
| 2014/0116458 A1 | 5/2014 | Krueger |
| 2014/0135414 A1 | 5/2014 | Loomis |
| 2014/0237732 A1 | 8/2014 | Zuedel Fernandes et al. |
| 2014/0261517 A1* | 9/2014 | Humphreys ............. A61K 8/35 132/204 |
| 2014/0302103 A1 | 10/2014 | Carter et al. |
| 2014/0356303 A1 | 12/2014 | Rocco et al. |
| 2014/0377206 A1 | 12/2014 | Uehara et al. |
| 2015/0011450 A1 | 1/2015 | Carter et al. |
| 2015/0030643 A1 | 1/2015 | Gartstein et al. |
| 2015/0093420 A1 | 4/2015 | Snyder et al. |
| 2015/0166253 A1* | 6/2015 | Nomura ................. B65B 31/003 222/402.1 |
| 2015/0190326 A1 | 7/2015 | Brouard et al. |
| 2015/0359725 A1 | 12/2015 | Glenn, Jr. et al. |
| 2015/0359726 A1 | 12/2015 | Glenn, Jr. et al. |
| 2015/0359727 A1 | 12/2015 | Glenn, Jr. et al. |
| 2015/0359728 A1 | 12/2015 | Glenn, Jr. et al. |
| 2016/0000673 A1 | 1/2016 | Ainger et al. |
| 2016/0310375 A1 | 4/2016 | Torres Rivera et al. |
| 2016/0310376 A1 | 4/2016 | Torres Rivera et al. |
| 2016/0143821 A1 | 5/2016 | Chang et al. |
| 2016/0309871 A1 | 10/2016 | Torres Rivera et al. |
| 2016/0310371 A1 | 10/2016 | Zhao et al. |
| 2016/0310372 A1 | 10/2016 | Glenn, Jr. et al. |
| 2016/0310377 A1 | 10/2016 | Torres Rivera et al. |
| 2016/0310397 A1 | 10/2016 | Johnson et al. |
| 2017/0087068 A1 | 3/2017 | Callens et al. |
| 2017/0165155 A1 | 6/2017 | Glenn, Jr. et al. |
| 2017/0165156 A1 | 6/2017 | Glenn, Jr. et al. |
| 2017/0165157 A1 | 6/2017 | Glenn, Jr. et al. |
| 2017/0165162 A1 | 6/2017 | Glenn, Jr. et al. |
| 2017/0165163 A1 | 6/2017 | Glenn, Jr. et al. |
| 2017/0165191 A1 | 6/2017 | Glenn, Jr. et al. |
| 2017/0174413 A1 | 6/2017 | Callens et al. |
| 2017/0304184 A1 | 10/2017 | Glenn, Jr. et al. |
| 2017/0304185 A1 | 10/2017 | Glenn, Jr. et al. |
| 2017/0304186 A1 | 10/2017 | Glenn, Jr. et al. |
| 2018/0168948 A1 | 6/2018 | Glenn, Jr. et al. |
| 2018/0168949 A1 | 6/2018 | Glenn, Jr. et al. |
| 2018/0168996 A1 | 6/2018 | Glenn, Jr. et al. |
| 2018/0221270 A1 | 8/2018 | Glenn, Jr. et al. |
| 2018/0256457 A1 | 9/2018 | Glenn, Jr. et al. |
| 2018/0256459 A1 | 9/2018 | Torres Rivera et al. |
| 2018/0256481 A1 | 9/2018 | Glenn, Jr. et al. |
| 2018/0353398 A1 | 12/2018 | Torres Rivera et al. |

FOREIGN PATENT DOCUMENTS

| | | |
|---|---|---|
| EP | 1002525 A2 | 5/2000 |
| EP | 1340485 A2 | 2/2003 |
| EP | 2138155 A2 | 12/2009 |
| EP | 2883533 A1 | 6/2015 |
| JP | H06227941 A | 8/1994 |
| JP | 2001302466 A | 10/2001 |
| JP | 3242689 B2 | 12/2001 |
| JP | 2003-119113 A | 4/2003 |
| JP | 2005232271 A | 9/2005 |
| JP | 2006182743 A | 7/2006 |
| JP | 2010-132569 A | 6/2010 |
| JP | 4694171 B2 | 6/2011 |
| JP | 2014-125477 A | 7/2014 |
| WO | WO 96/19188 A1 | 6/1996 |
| WO | WO 97/20626 A1 | 6/1997 |
| WO | WO0222085 A1 | 3/2002 |
| WO | WO 2004/078901 A1 | 9/2004 |
| WO | WO2006045170 A2 | 5/2006 |
| WO | WO 2013/176666 A1 | 11/2013 |

OTHER PUBLICATIONS

U.S. Appl. No. 15/380,345, filed Dec. 15, 2016, Glenn, Jr. et al.
U.S. Appl. No. 15/380,373, filed Dec. 15, 2016, Glenn, Jr. et al.
U.S. Appl. No. 15/492,429, filed Apr. 20, 2017, Glenn, Jr. et al.
U.S. Appl. No. 15/492,451, filed Apr. 20, 2017, Glenn, Jr. et al.
U.S. Appl. No. 15/492,469, filed Apr. 20, 2017, Glenn, Jr. et al.
U.S. Appl. No. 15/381,298, filed Dec. 16, 2016, Callens et al.
U.S. Appl. No. 62/435,267, filed Dec. 16, 2016, Glenn, Jr. et al.
U.S. Appl. No. 62/435,271, filed Dec. 16, 2016, Glenn, Jr. et al.
U.S. Appl. No. 62/435,296, filed Dec. 16, 2016, Glenn, Jr. et al.
All Office Actions, U.S. Appl. No. 14/739,588.

(56) References Cited

OTHER PUBLICATIONS

All Office Actions, U.S. Appl. No. 14/739,670.
All Office Actions, U.S. Appl. No. 14/739,708.
All Office Actions, U.S. Appl. No. 14/739,755.
All Office Actions, U.S. Appl. No. 15/135,684.
All Office Actions, U.S. Appl. No. 15/135,691.
All Office Actions, U.S. Appl. No. 15/135,705.
All Office Actions, U.S. Appl. No. 15/135,715.
All Office Actions, U.S. Appl. No. 15/380,194.
All Office Actions, U.S. Appl. No. 15/380,218.
All Office Actions, U.S. Appl. No. 15/380,261.
All Office Actions, U.S. Appl. No. 15/380,293.
All Office Actions, U.S. Appl. No. 15/380,345.
All Office Actions, U.S. Appl. No. 15/380,373.
All Office Actions, U.S. Appl. No. 15/274,226.
All Office Actions, U.S. Appl. No. 15/381,298.
All Office Actions, U.S. Appl. No. 15/136,020.
All Office Actions, U.S. Appl. No. 15/136,032.
All Office Actions, U.S. Appl. No. 15/492,429.
All Office Actions, U.S. Appl. No. 15/492,451.
All Office Actions, U.S. Appl. No. 15/492,469.
Carolyn Evans: "Scalp Cleansing, Scalp Tonique, Hair Shampoo, Hair Conditioner, Demonstration" Youtube, Apr. 22, 2012, p. 2. First part of the video (0-3 min) dedicated to "scalp cleansing"; second part of the video (3-6 min) dedicated to the treatment of the hair.
Anonymous: "GNPD—Anti-Dandruff Shampoo", Nov. 1, 2012.
Anonymous "Shampoo only Scalp? or entire head?—The Long Hair Community Discussion Boards", Feb. 1, 2011, Retrieved from the internet: URL: http://forums.longhaircommunity.com/archieve/index.php/t-91788.html, retrieved on Jul. 21, 2016.
Samantha Zabell: "Mistakes You're Making Washing Your Hair—How You're Washing Your Hair Wrong", Jan. 14, 2014, Retrieved from the Internet: URL: http://www.goodhousekeeping.com/beauty/hair/tips/a19894/mistakes-washing-your-hair/, Section 3. "Overdoing it on shampoo and/or conditioner"; p. 2, retrieved on Jul. 21, 2016.
Anonymous: "GNPD—Anti-Dandruff Shampoo + Conditioner Set", Procter and Gamble China, Apr. 1, 2009, Mintel GNPD, Retrieved from the Internet: URL: http://www.gnpd.com/sinatra/recordpage/107827/from_search/EkXVQ1u6vF/?page=2, Retrieved on Jul. 12, 2016.
Database GNPD, Mintel; Aug. 2014 "Gold Olive Haircare Set".
Database GNPD Mintel; May 2014, "Coconut & Macadamia Oil Nourishing Shampoo and Nourishing Conditioner".
"Clarifying Shampoo", Mintel, Jun. 2015.
"Reinforcing conditioner", Mintel, May 2014.
Silsoft* 251, amine functional silicone microemulsion, Momentive Marketing Bulletin, 2012, 2 pages.
In-Cosmetics 2012: Wacker Introduced Novel Silicone Emulsions and New Hybrid Polymer for Hair-Care and Hair-Styling Products, Apr. 17, 2012, Munich.
PCT International Search Report and Written Opinion for PCT/US2016/066753 dated Feb. 28, 2017, 11 pages.
PCT International Search Report and Written Opinion for PCT/US2016/067916 dated Mar. 29, 2016.
PCT International Search Report and Written Opinion for PCT/US2016/028731 dated Jul. 5, 2016, 11 pages.
PCT International Search Report and Written Opinion for PCT/US2016/028860 dated Jul. 7, 2016, 11 pages.
PCT International Search Report and Written Opinion for PCT/US2015/035796 dated Sep. 14, 2015, 9 pages.
PCT International Search Report and Written Opinion for PCT/US2015/035756 dated Dec. 21, 2015, 13 pages.
PCT International Search Report and Written Opinion for PCT/US2015/035797 dated Sep. 14, 2015, 9 pages.
PCT International Search Report and Written Opinion for PCT/US2015/035799 dated Sep. 14, 2015, 9 pages.
PCT International Search Report and Written Opinion for PCT/US2016/028739 dated Jul. 4, 2016, 11 pages.
PCT International Search Report and Written Opinion for PCT/US2016/066755 dated Feb. 27, 2017, 12 pages.
PCT International Search Report and Written Opinion for PCT/US2016/066759 dated Feb. 27, 2017, 11 pages.
PCT International Search Report and Written Opinion for PCT/US2016/066754 dated Feb. 20, 2017, 11 pages.
PCT International Search Report and Written Opinion for PCT/US2016/028745 dated Aug. 8, 2016.
PCT International Search Report and Written Opinion for PCT/US2016/028853 dated Sep. 30, 2016, 19 pages.
PCT International Search Report and Written Opinion for PCT/US2016/028855, dated Oct. 5, 2016, 18 pages.
PCT International Search Report and Written Opinion for PCT/US2016/028743 dated Jul. 25, 2016.
U.S. Appl. No. 15/843,069, filed Dec. 15, 2017, Glenn, Jr. et al.
U.S. Appl. No. 15/843,146, filed Dec. 15, 2017, Glenn, Jr. et al.
U.S. Appl. No. 15/843,178, filed Dec. 15, 2017, Glenn, Jr. et al.
All final and non-final office actions for U.S. Appl. No. 15/843,069.
All final and non-final office actions for U.S. Appl. No. 15/843,146.
All final and non-final office actions for U.S. Appl. No. 15/843,178.
Fabida. https://makeupandbeauty.com/head-shoulders-anti-dandruff-itchy-scalu-care-shampoo-review/. Published Jun. 26, 2012.
Free Sample. https://web.archive.org/web/20111116042029/http://freesampleprincess.com/head-and-shoulders-itchy-scalp-care-free-sample. Published Nov. 16, 2011.
Hair Conditioner Tips and Tricks. https://web.archive.org/web/20121106125731/http://www.thehairstyler.com/features/articles/hair-care/hair-conditioner-tips-and-tricks. Published Nov. 6, 2012.
Mommy Story, http://www.amommystory.com/2011/11/head-shoulders-eucalyptus-itchy-scalp-care-to-the-rescue-review-giveaway.html. Published Nov. 21, 2011.
PCT International Search Report and Written Opinion for PCT/US2017/028472 dated Jun. 29, 2017.
PCT International Search Report and Written Opinion for PCT/US2017/028473 dated Jun. 29, 2017.
PCT International Search Report and Written Opinion for PCT/US2017/028474 dated Jun. 29, 2017.
Stylecaster. http://stylecaster.com/beauty/how-to-get-rid-of-dandruff/. Published: Jan. 16, 2014.
Xiameter Mem-0949 Emulsion (Nov. 2011).
All final and non-final office actions for U.S. Appl. No. 15/946,275.
All final and non-final office actions for U.S. Appl. No. 15/973,845.
All final and non-final office actions for U.S. Appl. No. 15/978,667.
All final and non-final office actions for U.S. Appl. No. 16/104,343.
All final and non-final Office Actions, U.S. Appl. No. 15/135,715.
PCT International Search Report and Written Opinion for PCT/US2017/066561 dated Apr. 4, 2018.
PCT International Search Report and Written Opinion for PCT/US2017/066563 dated Apr. 4, 2018.

* cited by examiner

HAIR CARE CONDITIONING COMPOSITION

FIELD OF THE INVENTION

The present invention relates to a hair care composition comprising a cationic surfactant, a silicone, and an aqueous carrier wherein the viscosity is lower than about 500 centipoise and the composition is substantially free of fatty alcohols.

BACKGROUND OF THE INVENTION

Today's hair conditioners almost universally comprise high levels of high melting point fatty compounds, the most common of which are C16 to C18 fatty alcohols. These high melting point fatty compounds are employed as structuring agents wherein they are combined with one or more surfactants and an aqueous carrier to form a gel network. The gel network provides a viscous and high yield point rheology which facilitates the dispensing of the conditioner from a bottle or tube and the subsequent distribution and spreading of the product through the hair by the consumer. The gel network structuring also enables incorporation of silicones, perfumes and oils in the form of an oil-in-water emulsion that is phase stable. These silicones and oils are intended to be deposited on the hair to provide the primary hair care benefits including wet and dry combing friction reduction and hair manageability etc.

This invention relates to high purity concentrated rinse-off hair care compositions with a high content of silicone and a silicone-to-high melting point fatty compound ratio of about 100:0. The composition provides consumer acceptable wet and dry conditioning feel along with good product phase stability at low viscosity (lower than about 500 cP) while remaining substantially free of a high melt fatty compound. The hair care composition can be delivered in various forms such as: aerosol foamed, mechanical (e.g. pump and squeeze) foamed, concentrated liquid, and pre-aerated foam etc.

Current gel network hair conditioners can lead to excessive co-deposits of the high melting point fatty compound on the hair over multiple cycles. Additionally, the deposited high melting point fatty compounds can build-up on hair over multiple cycles and lead to waxy build-up on hair and hair weigh down. Indeed, one of the major consumer complaints with hair conditioners is waxy residue which makes hair look greasy or feel heavy. Many current gel network hair conditioners deposit up to 10 times more high melting point fatty compounds (fatty alcohols) than silicone or oil after approximately 10 treatment cycles in technical testing. While not being bound to theory, this is hypothesized to be due to the greater than about ten times concentration of high melting point weight fatty compounds in the product relative to the silicone or oil. Importantly, such a high level of melting point fatty compounds such as fatty alcohols, is useful to produce a shelf stable gel network with sufficient structuring for consumer acceptable viscosity and rheology.

Typically, silicone conditioning agents alone do not reduce wet friction enough to provide sufficient wet feel. Therefore, there is a need to deliver consumer acceptable wet feel via a hair care composition without fatty alcohols (or gel network).

Described herein is a hair care composition that enables new product opportunities and consumer benefits by addressing the current disadvantages associated with gel network conditioners. Is has been found that concentrated and low viscosity hair conditioner compositions can be delivered to the hair in foamed form. These hair care compositions enable sufficient dosage from a foam delivery form while also minimizing the need for product stabilizing with high melting point fatty compounds or other "insoluble" structurants that can lead to significant co-deposits, build-up and weigh down of hair. The net result has been a step change improvement in silicone deposition purity versus today's rinse-off products and an improvement in technical performance benefits from such a pure and transparent deposited silicone layer. These benefits include multi-cycle hair care without hair weigh down, durable conditioning, reduced hair dye fade, and increased color vibrancy.

SUMMARY OF THE INVENTION

Described herein is a hair care composition suitable for mechanical and aerosol foaming comprising: from about 4% to about 20% by weight of one or more silicones, wherein the particle size of the one or more silicones is from about 1 nm to about 300 nm, from about 0.1% to about 5% by weight of a cationic surfactant wherein the cationic surfactant has carbon chains of C20 and higher; alternatively between C20 and C40, and an aqueous carrier; wherein the hair care composition has a liquid phase viscosity of from about 1 centipoise to about 500 centipoise; and wherein the hair care composition comprises between 0% and about 0.2% fatty alcohol. The hair care composition described herein wherein the silicone is an emulsion with a particle size of less than about 100 nm. The hair care composition described herein having from about 0.2% to about 4% by weight of a cationic surfactant wherein the cationic surfactant has carbon chains of C20 and higher, alternatively having from about 0.5% to about 3.5% by weight of a cationic surfactant wherein the cationic surfactant has carbon chains of C20 and higher, alternatively having from about 0.5% to about 2.5% by weight of a cationic surfactant wherein the cationic surfactant has carbon chains between C20 and C40.

The hair care composition described herein, wherein the cationic surfactant is selected from the group consisting of behentrimonium chloride, behentrimonium methosulfate, behenamidopropyl dimethylamine, and mixtures thereof. The hair care composition described herein wherein the composition further comprises from about 0.2% to about 3% of di-fatty alkyl quaternary ammonium salt having a molecular structure of: $(CH_3)_2$-$R_1R_2NH_4$+$X$- wherein $R_1$ and $R_2$ are alkyl groups with carbon chains between C12 and C20 and wherein $X$- is an inorganic or organic anion.

The hair care composition of described herein, comprising from about 0.5% to about 2.5% by weight, of di-fatty alkyl quaternary ammonium salt, alternatively comprising from about 0.5% to about 2% of di-fatty alkyl quaternary ammonium salt; wherein the di-fatty alkyl quaternary ammonium salt is selected from the group consisting of distearyldimonium chloride, dicetyldimonium chloride, and mixtures thereof.

The hair care composition described herein may further comprise from about 2% to about 20% by weight of water miscible glycols, alternatively from about 3% to about 18% by weight of water miscible glycols, alternatively from about 5% to about 15% by weight of water miscible glycols. The water miscible glycols can be glycerin.

The hair care composition described herein may further comprise from about 0.01% to about 0.8% by weight of a water-soluble polymer, wherein the water soluble polymer has a molecular weight of less than about 100,000 g/mol. The water soluble polymers can be selected from the group consisting of polyethylene oxide, polyvinylpyrrolidone and mixtures thereof.

The hair care composition may further comprise from about 1% to about 10% by weight of an aerosol propellant, alternatively from about 2% to about 8% by weight of an aerosol propellant, and alternatively from about 3% to about 6% by weight of an aerosol propellant. The aerosol propellant can be selected from the group consisting of hydrocarbon mixtures of butane, isobutane and propane, and hydrofluoroolefins.

The hair care composition can be in the form of a foam. The foam can be dispensed via a mechanical or aerosol foam dispenser.

DETAILED DESCRIPTION OF THE INVENTION

While the specification concludes with claims particularly pointing out and distinctly claiming the invention, it is believed that the present invention will be better understood from the following description.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "M.Wt." refers to the weight average molecular weight unless otherwise stated. Molecular weight is measured using industry standard method, gel permeation chromatography ("GPC").

As used herein, the terms "include," "includes," and "including," are meant to be non-limiting and are understood to mean "comprise," "comprises," and "comprising," respectively.

As used herein, the term "concentrated" means a hair care composition comprising from about 4% to about 20% of one or more silicones, by weight of the hair care composition.

As used herein, the term "nanoemulsion" means an oil-in-water (o/w) emulsion with an average particle size ranging from about 1 nm to about 100 nm. The particle size referred to herein is z-average measured by dynamic light scattering. The nanoemulsion described herein may be prepared by the following methods: (1) mechanically breaking down the emulsion droplet size; (2) spontaneously forming the emulsion (may be referred to as a microemulsion in the literature); and (3) using emulsion polymerization to achieve average particle size in the target range described herein.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Where amount ranges are given, these are to be understood as being the total amount of said ingredient in the composition, or where more than one species fall within the scope of the ingredient definition, the total amount of all ingredients fitting that definition, in the composition.

For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the hair care composition.

Hair Care Composition

The hair care composition provides good wet and dry conditioning feel along with good product phase stability, good lather, low viscosity (lower than about 500 cP), excellent foam quality (when delivered via a foaming dispenser including, but not limited to, an aerosol, pump or squeeze foam dispenser). The hair care composition comprises a cationic surfactant, a silicone, an aqueous carrier, and has a liquid phase viscosity of from about 1 cps to about 500 cps, and further wherein the hair care composition has a silicone to high melting point fatty alcohol ratio of about 100:0.

A. Cationic Surfactants

The hair care composition comprises from about 0.1% to about 5% by weight, from about 0.2% to about 4.5% by weight, from about 0.2% to about 4% by weight, from about 0.5% to about 3.5% by weight, from about 0.5% to about 3% by weight, or from about 0.5% to about 2.5% by weight of cationic surfactants with carbon chains with C20 and higher; alternatively between C20 and C40.

The resulting composition is phase stable in the long term even though the cationic surfactant has a relatively long carbon chains (greater than about C20). Additionally, the cationic surfactant contributes to the wet feel by providing a slippery effect during use without negative hair weigh down when dry.

The cationic surfactant may be a mono-long alkyl quaternized ammonium salt having the formula (XIII) [from WO2013148778]:

(XIII)

wherein one of $R^{71}$, $R^{72}$ $R^{73}$ a n $R^{74}$ selected from an aliphatic group of from about 14 to about 30 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$ $R^{73}$ and $R^{74}$ are independently selected from an aliphatic group of from about 1 to about 8 carbon atoms or an aromatic, alkoxy, polyoxyalkylene, alkylamido, hydroxyalkyl, aryl or alkylaryl group having up to about 8 carbon atoms; and X is a salt-forming anion such as those selected from halogen, (e.g., chloride, bromide), acetate, citrate, lactate, glycolate, phosphate, nitrate, sulfonate, sulfate, alkylsulfate, glutamate, and alkyl sulfonate radicals. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. One of $R^{71}$, $R^{72}$ $R^{73}$ and $R^{74}$ can be selected from an alkyl group of from about 14 to about 30 carbon atoms, alternatively from about 16 to about 22 carbon atoms, alternatively from about 16 to about 18 carbon atoms; the remainder of $R^{71}$, $R^{72}$, $R^{73}$, and $R^{74}$ are independently selected from the group consisting of $CH_3$, $C_2H_5$, $C_2H_4OH$, $CH_2C_5H_5$, and mixtures thereof; and (X) is selected from the group consisting of Cl, Br, $CH_3OSO_3$, and mixtures thereof. It is believed that such mono-long alkyl quaternized ammonium salts can provide improved slippery and slick feel on wet hair.

Nonlimiting examples of such mono-long alkyl quaternized ammonium salt cationic surfactants include: behenyl trimethyl ammonium chloride available, for example, with tradename Genamine KDMP from Clariant, with tradename INCROQUAT TMC-80 from Croda and ECONOL TM22 from Sanyo Kasei; stearyl trimethyl ammonium chloride available, for example, with tradename CA-2450 from Nikko Chemicals; cetyl trimethyl ammonium chloride available, for example, with tradename CA-2350 from Nikko Chemicals; behenyltrimethylammonium methyl sulfate, available from FeiXiang; hydrogenated tallow alkyl trimethyl ammonium chloride; stearyl dimethyl benzyl ammonium chloride; and stearoyl amidopropyl dimethyl benzyl ammonium chloride.

Among them, suitable cationic surfactants include, but are not limited to, those having a shorter alkyl group, i.e., $C_{16}$ alkyl group. Such cationic surfactant includes, for example, cetyl trimethyl ammonium chloride. It is believed that cationic surfactants having a shorter alkyl group are advantageous for hair care compositions comprising a cationic surfactant and with improved shelf stability.

Suitable cationic surfactants include, but are not limited to, behentrimonium chloride, behentrimonium methosulfate, behenamidopropyl dimethylamine, and mixtures thereof.

B. Silicone

The hair care composition can comprise from about 4% to about 20% by weight, alternatively from about 6% to about 18% by weight; and alternatively from about 8% to about 16% by weight of one of more silicones with a particle size of less than about 300 nm, alternatively less than about 200 nm, and alternatively less than about 100 nm. The silicone can be in the form of a nanoemulsion.

The particle size of the one or more silicones may be measured by dynamic light scattering (DLS). A Malvern Zetasizer Nano ZEN3600 system (www.malvern.com) using He—Ne laser 633 nm may be used for the measurement at 25° C.

The autocorrelation function may be analyzed using the Zetasizer Software provided by Malvern Instruments, which determines the effective hydrodynamic radius, using the Stokes-Einstein equation:

$$D = \frac{k_B T}{6\pi\eta R}$$

wherein $k_B$ is the Boltzmann Constant, T is the absolute temperature, $\eta$ is the viscosity of the medium, D is the mean diffusion coefficient of the scattering species, and R is the hydrodynamic radius of particles.

Particle size (i.e. hydrodynamic radius) may be obtained by correlating the observed speckle pattern that arises due to Brownian motion and solving the Stokes-Einstein equation, which relates the particle size to the measured diffusion constant, as is known in the art.

For each sample, 3 measurements may be made and Z-average values may be reported as the particle size.

The one or more silicones may be in the form of a nanoemulsion. The nanoemulsion may comprise any silicone suitable for application to the skin and/or hair.

The one or more silicones may include in their molecular structure polar functional groups such as Si—OH (present in dimethiconols), primary amines, secondary amines, tertiary amines, and quaternary ammonium salts. The one or more silicones may be selected from the group consisting of aminosilicones, pendant quaternary ammonium silicones, terminal quaternary ammonium silicones, amino polyalkylene oxide silicones, quaternary ammonium polyalkylene oxide silicones, and amino morpholino silicones.

The one or more silicones may comprise:
(a) at Least One Aminosilicone Corresponding to Formula (V):

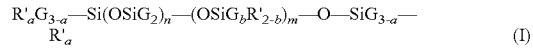
(I)

in which:
G is chosen from a hydrogen atom, a phenyl group, OH group, and $C_1$-$C_8$ alkyl groups, for example methyl,
a is an integer ranging from 0 to 3, and in one embodiment a is 0,
b is chosen from 0 and 1, and in one embodiment b is 1,
m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10;
R' is a monovalent group of formula —$C_qH_{2q}$L in which q is a number from 2 to 8 and L is an optionally quaternized amine group chosen from the groups:

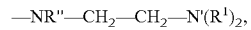

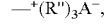

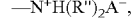

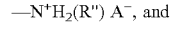

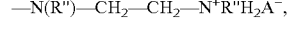

in which R" can be chosen from a hydrogen atom, phenyl groups, benzyl groups, and saturated monovalent hydrocarbon-based groups, such as for example an alkyl group comprising from 1 to 20 carbon atoms, and $A^-$ is chosen from halide ions such as, for example, fluoride, chloride, bromide and iodide.

The one or more silicones may include those corresponding to formula (1) wherein a=0, G=methyl, m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10; and L is —N(CH$_3$)$_2$ or —NH$_2$, alternatively —NH$_2$.

Additional said at least one aminosilicone of the invention include:

(b) Pendant Quaternary Ammonium Silicones of Formula (VII):

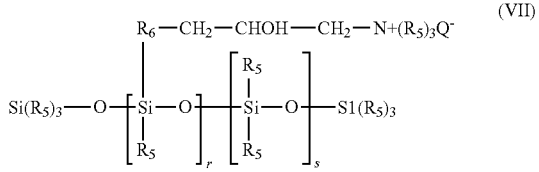

in which:
- R$_5$ is chosen from monovalent hydrocarbon-based groups comprising from 1 to 18 carbon atoms, such as C$_1$-C$_{18}$ alkyl groups and C$_2$-C$_{18}$ alkenyl groups, for example methyl;
- R$_6$ is chosen from divalent hydrocarbon-based groups, such as divalent C$_1$-C$_{18}$ alkylene groups and divalent C$_1$-C$_{18}$ alkylenoxy groups, for example C$_1$-C$_8$ alkylenoxy groups, wherein said R$_6$ is bonded to the Si by way of an SiC bond;
- Q$^-$ is an anion that can be for example chosen from halide ions, such as chloride, and organic acid salts (such as acetate);
- r is an average statistical value ranging from 2 to 20, such as from 2 to 8;
- s is an average statistical value ranging from 20 to 200, such as from 20 to 50.

Such aminosilicones are described more particularly in U.S. Pat. No. 4,185,087, the disclosure of which is incorporated by reference herein.

A silicone which falls within this class is the silicone sold by the company Union Carbide under the name "Ucar Silicone ALE 56".

Further examples of said at least one aminosilicone include:

c) Quaternary Ammonium Silicones of Formula (VIIb):

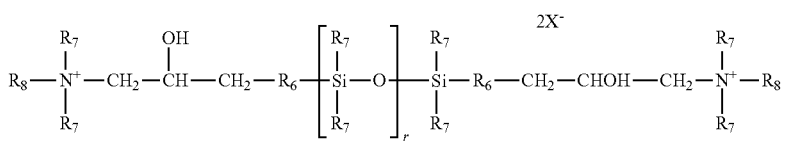

in which:
- groups R$_7$, which may be identical or different, are each chosen from monovalent hydrocarbon-based groups comprising from 1 to 18 carbon atoms, such as C$_1$-C$_{18}$ alkyl groups, for example methyl, C$_2$-C$_{18}$ alkenyl groups, and rings comprising 5 or 6 carbon atoms;
- R$_6$ is chosen from divalent hydrocarbon-based groups, such as divalent C$_1$-C$_{18}$ alkylene groups and divalent C$_1$-C$_{18}$ alkylenoxy, for example C$_1$-C$_8$, group connected to the Si by an SiC bond;
- R$_8$, which may be identical or different, represent a hydrogen atom, a monovalent hydrocarbon-based group comprising from 1 to 18 carbon atoms, and in particular a C$_1$-C$_{18}$ alkyl group, a C$_2$-C$_{18}$ alkenyl group or a group —R$_6$—NHCOR$_7$;
- X$^-$ is an anion such as a halide ion, in particular chloride, or an organic acid salt (acetate, etc.);
- r represents an average statistical value from 2 to 200 and in particular from 5 to 100.

Such silicones are described, for example, in application EP-A-0 530 974, the disclosure of which is incorporated by reference herein.

Silicones falling within this class are the silicones sold by the company Eovnik under the names Abil Quat 3270, Abil Quat 3272, Abil Quat 3474 and Abil ME 45.

Further examples of said at least one aminosilicone include:

d) Quaternary Ammonium and Polyalkylene Oxide Silicones wherein the quaternary nitrogen groups are located in the polysiloxane backbone, at the termini, or both.

Such silicones are described in PCT Publication No. WO 2002/010257, the disclosure of which is incorporated by reference herein.

Silicones falling within this class are the silicones sold by the company Momentive under the names Silsoft Q . . .

(e) Aminofunctional Silicones Having Morpholino Groups of Formula (V):

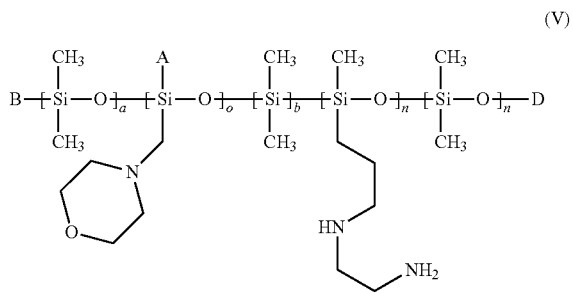

in which

A denotes a structural unit (I), (II), or (III) bound via —O—

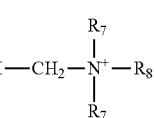

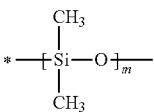

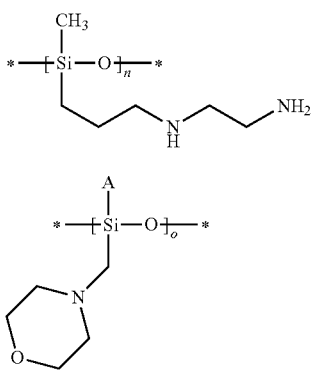

(II)

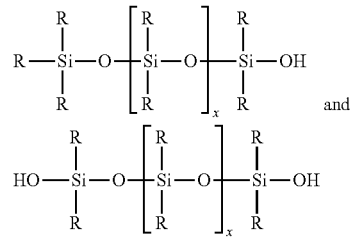

(III)

or an oligomeric or polymeric residue, bound via —O—, containing structural units of formulas (I), (II), or (III), or half of a connecting oxygen atom to a structural unit (III), or denotes —OH,

* denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers between 0 and 1000, with the provision that a+b+c>0, m, n, and o denote integers between 1 and 1000.

Aminofunctional silicones of this kind bear the INCI name: Amodimethicone/Morpholinomethyl Silsesquioxane Copolymer. A particularly suitable amodimethicone is the product having the commercial name Wacker Belsil® ADM 8301E.

Examples of such silicones are available from the following suppliers:
offered by the company Dow Corning: Fluids: 2-8566, AP 6087, AP 6088, DC 8040 Fluid, fluid 8822A DC, DC 8803 & 8813 polymer, 7-6030, AP-8104, AP 8201; Emulsions: CE-8170 AF Micro Emulsion, 2-8177, 2-8194 Microemulsion, 9224 Emulsion, 939, 949, 959, DC 5-7113 Quat Microemulsion, DC 5-7070 Emulsion, DC CE-8810, CE 8401 Emulsion, CE 1619, Dow Corning Toray SS-3551, Dow Corning Toray SS-3552;
offered by the company Wacker: Wacker Belsil ADM 652, ADM 656, 1100, 1600, 1650 (fluids) ADM 6060 (linear amodimethicone) emulsion; ADM 6057 E (branched amodimethicone) emulsion; ADM 8020 VP (micro emulsion); SLM 28040 (micro emulsion); offered by the Company Momentive:Silsoft 331, SF1708, SME 253 & 254 (emulsion), SM2125 (emulsion), SM 2658 (emulsion), Silsoft Q (emulsion) offered by the company Shin-Etsu:KF-889, KF-8675, KF-8004, X-52-2265 (emulsion); offered by the Company Siltech Silicones:Siltech E-2145, E-Siltech 2145-35; offered by the company Evonik Industries:Abil T Quat 60th Some non-limiting examples of aminosilicones include the compounds having the following INCI names: Silicone Quaternium-1, Silicone Quaternium-2, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-17, Silicone Quaternium-18, Silicone Quaternium-20, Silicone Quaternium-21, Silicone Quaternium-22, Quaternium-80, as well as Silicone Quaternium-2 Panthenol Succinate and Silicone Quaternium-16/Glycidyl Dimethicone Crosspolymer.

The amino silicones can be supplied in the form of a nanoemulsion and include MEM 9049, MEM 8177, MEM 0959, MEM 8194, SME 253, and Silsoft Q.

The one or more silicones may include dimethicones, and/or dimethiconols. The dimethiconols are hydroxyl terminated dimethylsilicones represented by the general chemical formulas $$R-\underset{\underset{R}{|}}{\overset{\overset{R}{|}}{Si}}-O-\left[\underset{\underset{R}{|}}{\overset{\overset{R}{|}}{Si}}-O\right]_x-\underset{\underset{R}{|}}{\overset{\overset{R}{|}}{Si}}-OH \quad \text{and}$$

$$HO-\underset{\underset{R}{|}}{\overset{\overset{R}{|}}{Si}}-O-\left[\underset{\underset{R}{|}}{\overset{\overset{R}{|}}{Si}}-O\right]_x-\underset{\underset{R}{|}}{\overset{\overset{R}{|}}{Si}}-OH$$

wherein R is an alkyl group (R can be methyl or ethyl) and x is an integer up to about 500, chosen to achieve the desired molecular weight. Commercial dimethiconols typically are sold as mixtures with dimethicone or cyclomethicone (e.g., Dow Corning® 1401, 1402, and 1403 fluids).

C. Nonionic Emulsifiers

The concentrated hair care composition may comprise from about 3% to about 20%, alternatively from about 5% to about 15%, and alternatively from about 7.5% to about 12% of a nonionic emulsifier, by weight of the concentrated hair care composition. The one or more silicones may be supplied in the form of a nanoemulsion comprising a nonionic emulsifier. Nonionic emulsifiers may be broadly defined as including compounds containing an alkylene oxide groups (hydrophilic in nature) with a hydrophobic compound, which may be aliphatic or alkyl aromatic in nature. Suitable examples of nonionic emulsifiers include, but are not limited to:

1. Alcohol ethoxylates which are condensation products of aliphatic alcohols having from about 8 to about 18 carbon atoms, in either straight chain or branched chain configuration, with from about 2 to about 35 moles of ethylene oxide, e.g., a coconut alcohol ethylene oxide condensate having from about 2 to about 30 moles of ethylene oxide per mole of coconut alcohol, the coconut alcohol fraction having from about 10 to about 14 carbon atom.

2. The polyethylene oxide condensates of alkyl phenols, e.g., the condensation products of the alkyl phenols having an alkyl group containing from about 6 to about 20 carbon atoms in either a straight chain or branched chain configuration, with ethylene oxide, the said ethylene oxide being present in amounts equal to from about 3 to about 60 moles of ethylene oxide per mole of alkyl phenol.

3. Those derived from the condensation of ethylene oxide with the product resulting from the reaction of propylene oxide and ethylene diamine products.

4. Long chain tertiary amine oxides such as those corresponding to the following general formula: R1 R2 R3 N-->O wherein R1 contains an alkyl, alkenyl or monohydroxy alkyl redical of from about 8 to about 18 carbon atoms, from 0 to about 10 ethylene oxide moieties, and from 0 to about 1 glyceryl moiety, and R2 and R3 contain from about 1 to about 3 carbon atoms and from 0 to about 1 hydroxy group, e.g., methyl, ethyl, propyl, hydroxyethyl, or hydroxypropyl radicals (the arrow in the formula represents a semipolar bond).

5. Long chain tertiary phosphine oxides corresponding to the following general formula: RR'R"P-->O wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing about 1 to about 3 carbon atoms. The arrow in the formula represents a semipolar bond.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety.

7. Polysorbates, e.g., sucrose esters of fatty acids, Such materials are described in U.S. Pat. No. 3,480,616, e.g., sucrose cocoate (a mixture of sucrose esters of a coconut acid, consisting primarily of monoesters, and sold under the tradenames GRILLOTEN LSE 87K from RITA, and CRODESTA SL-40 from Croda).

8. Alkyl polysaccharide nonionic emulsifiers are disclosed in U.S. Pat. No. 4,565,647, Llenado, issued Jan. 21, 1986, having a hydrophobic group containing from about 6 to about 30 carbon atoms, from about 10 to about 16 carbon atoms and a polysaccharide, e.g., a polyglycoside, hydrophilic group. The polysaccharide can contain from about 1.0 to about 10, preferably from about 1.3 to about 3, alternatively from about 1.3 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units. Optionally there can be a polyalkyleneoxide chain joining the hydrophobic moiety and the polysaccharide moiety. The alkyl group can contain up to about 3 hydroxy groups and/or the polyalkyleneoxide chain can contain up to about 10, alternatively less than 5, alkylene moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses.

9. Polyethylene glycol (PEG) glyceryl fatty esters, as depicted by the formula RC(O)OCH2 CH(OH)CH2 (OCH2 CH2)n OH wherein n is from about 5 to about 200, from about 20 to about 100, from about 30 to about 85, and RC(O)— is an ester wherein R comprises an aliphatic radical having from about 7 to 19 carbon atoms, from about 9 to 17 carbon atoms, from about 11 to 17 carbon atoms, from about 11 to 14 carbon atoms. The combinations of n may be from about 20 to about 100, with C12-C18, alternatively C12-C15 fatty esters, for minimized adverse effect on foaming.

The nonionic emulsifier may be a silicone emulsifier. A wide variety of silicone emulsifiers may be useful herein. These silicone emulsifiers are typically organically modified siloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other suitable examples include alkyl-modified dimethicone copolyols, i.e., compounds which contain C2-C30 pendant side chains. Still other useful dimethicone copolyols include materials having various cationic, anionic, amphoteric, and zwitterionic pendant moieties.

The nonionic emulsifier may have a hydrocarbon chain length of from about 16 to about 20 carbon atoms and from about 20 to about 25 moles of ethoxylate.

The nonionic emulsifier may have a hydrocarbon chain length of from about 19 to about 11 carbon atoms, alternatively from about 9 to about 11 carbon atoms, and from about 2 to about 4 moles of ethoxylate.

The nonionic emulsifier may comprise a combination of (a) a nonionic emulsifier having a hydrocarbon chain that is branched, has a length of from about 11 to about 15 carbon atoms, and has from about 5 to about 9 moles of ethoxylate; and (b) a nonionic emulsifier having a hydrocarbon chain that has a length of from about 11 to about 13 carbon atoms and has from about 9 to about 12 moles of ethoxylate.

The nanoemulsions used in this invention may be prepared by two different methods: (1) mechanical, and (2) emulsion polymerization.

The first method of preparing the nanoemulsion is the mechanical method in which the nanoemulsion is prepared via the following steps: (1) a primary surfactant is dissolved in water, (2) a silicone is added, and a two-phase mixture is formed, (3) with simple mixing, a co-surfactant is slowly added to the two-phase mixture, until a clear isotropic microemulsion of a siloxane-in-water is formed.

The second method of preparing the nanoemulsion is by emulsion polymerization. Polymer precursors, i.e., monomers, or reactive oligomers, which are immiscible in water; a surfactant to stabilize polymer precursor droplets in water; and a water soluble polymerization catalyst. Typically, the catalyst is a strong mineral acid such as hydrochloric acid, or a strong alkaline catalyst such as sodium hydroxide. These components are added to water, the mixture is stirred, and polymerization is allowed to advance until the reaction is complete, or the desired degree of polymerization (DP) is reached, and an emulsion of the polymer is formed.

The nonionic emulsifier in the formulation can have a hydrocarbon chain length of 16-20 and 20-25 ethoxylate mole.

The hydrocarbon chain length and the ethoxylate mole number for the nonionic emulsifier can be 9-11 and 2-4, respectively.

The nonionic emulsifier system may consists of a) C11-15 with 5-9 ethoxylate moles in branched configuration b) linear nonionic emulsifier with C11-13 hydrocarbon chain length and 9-12 moles of ethoxylate.

D. Aqueous Carrier

The hair care composition will typically comprise an aqueous carrier, which is present at a level of from about 40 wt % to about 95 wt %, or from about 45 wt % to about 90 wt %, or from about 50 wt % to about 85 wt %. The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier useful in the present invention includes water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

The hair care compositions may have a pH in the range from about 2 to about 10, at 25° C. Alternatively, the hair care composition has a pH in the range from about −4 to about 7, which may help to solubilize minerals and redox metals already deposited on the hair. Thus, the hair care composition can also be effective toward washing out the existing minerals and redox metals deposits, which can reduce cuticle distortion and thereby reduce cuticle chipping and damage.

E. Di-Fatty Alkyl Quaternary Ammonium Salts

Di-fatty alkyl quaternary ammonium salts may be added to improve wet feel without increasing hair weight down when the hair is dry. Di-fatty alkyl quaternary ammonium salts can be added at levels of from about 0.2% to about 3% by weight, from about 0.5% to about 2.5% by weight, and/or from about 0.5% to about 2% by weight of the hair care composition. These di-fatty alkyl quaternary ammonium salts can have a molecular structure of:

(CH3)2-R1R2NH4+X− wherein R1 and R2 are alkyl groups with carbon chains between C12 and C20 (C14 to C18; C16 to C18) and wherein X− is an inorganic or organic anion.

F. Mono-Alkyl Quaternary Ammonium Salts

Mono-alkyl quaternary ammonium salts may be added to improve the lather quality of the product during use. Mono-alkyl quaternary ammonium salts can be added at levels of from about 0.5% to about 5% by weight, from about 0.5% to about 4% by weight, from about 0.5% to about 3% by weight, and/or from about 1% to about 2.5% by weight of the hair care composition. The mono-fatty alkyl quaternary ammonium salts can have a molecular structure of

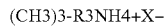
(CH3)3-R3NH4+X− wherein R3 is alkyl groups with carbon chains between C12 and C18 (C14 to C16); and wherein X− is an inorganic or organic anion.

G. Glycerin

Addition of from about 2 to about 20% (alternatively from about 3 to about 18%, alternatively from about 5 to about 15%) glycerin into the above composition surprisingly improves foam stability and elasticity after dispensing from the package before use (in the cases of aerosol, pump- and squeeze foam dispenser). The addition of glycerin also improves creaminess of lather and smooth wet feel during use. Surprisingly, addition of similar amount of dipropylene glycol into the composition can negatively affect foam stability and elasticity.

H. Water Soluble Polymers

The hair care composition may further comprise from about 0.01% to about 0.8% by weight, from about 0.05% to about 0.6% by weight, and/or from about 0.1% to about 0.5% by weight water-soluble polymers such as polyethylene oxide or polyvinylpyrrolidone wherein the water soluble polymer has a molecular weight of about 100,000 g/mol or less. The water soluble polymer can have a molecular weight of from about 1,000 to about 100,000 g/mol, alternatively from about 2,000 to about 90,000 g/mol, and alternatively from about 3,000 to about 80,000.

Suitable water soluble polymers include, but are not limited to (1) vegetable based polymers such as gum Arabic, tragacanth gum, galactan, guar gum, carob gum, karaya gum, carrageenan, pectin, agar, quince seed, algal colloid, starch (rice, corn, potato, or wheat), and glycyrrhizinic acid; (2) microorganism-based polymers such as xanthan gum, dextran, succinoglucan, and pullulan; and (3) animal-based polymers such as collagen, casein, albumin, and gelatin. Examples of semi-synthetic water-soluble polymers include (1) starch-based polymers such as carboxymethyl starch and methylhydroxypropyl starch; (2) cellulose-based polymers such as methylcellulose, nitrocellulose, ethylcellulose, methylhydroxypropylcellulose, hydroxyethylcellulose, sodium cellulose sulfate, hydroxypropylcellulose, sodium carboxymethylcellulose (CMC), crystalline cellulose, and cellulose powder; and (3) alginate-based polymers such as sodium alginate and propylene glycol alginate. Examples of synthetic water-soluble polymers include (1) vinyl-based polymers such as polyvinyl alcohol, polyvinyl methyl ether-based polymer, polyvinylpyrrolidone, and carboxyvinyl polymer (CARBOPOL 940, CARBOPOL 941; (2) polyoxyethylene-based polymers such as polyethylene glycol 20,000, polyethylene glycol 6,000, and polyethylene glycol 4,000; (3) copolymer-based polymers such as a copolymer of polyoxyethylene and polyoxypropylene, and PEG/PPG methyl ether; (4) acryl-based polymers such as poly(sodium acrylate), poly(ethyl acrylate), polyacrylamide, polyethylene imines, and cationic polymers. The water-swellable clay minerals are nonionic water-soluble polymers and correspond to one type of colloid-containing aluminum silicate having a triple layer structure. More particular, as examples thereof, mention may be made of bentonite, montmorillonite, beidellite, nontronite, saponite, hectorite, aluminum magnesium silicate, and silicic anhydride.

Examples of cationic water soluble polymers include, but are not limited to (1) quaternary nitrogen-modified polysaccharides such as cation-modified cellulose, cation-modified hydroxyethylcellulose, cation-modified guar gum, cation-modified locust bean gum, and cation-modified starch; (2) dimethyldiallylammonium chloride derivatives such as a copolymer of dimethyldiallylammonium chloride and acrylamide, and poly(dimethylmethylene piperidinium chloride); (3) vinylpyrrolidone derivatives such as a salt of a copolymer of vinylpyrrolidone and dimethylaminoethyl methacrylic acid, a copolymer of vinylpyrrolidone and methacrylamide propyltrimethylammonium chloride, and a copolymer of vinylpyrrolidone and methylvinylimidazolium chloride; and (4) methacrylic acid derivatives such as a copolymer of methacryloylethyldimethylbetaine, methacryloylethyl trimethylammonium chloride and 2-hydroxyethyl methacrylate, a copolymer of methacryloylethyldimethylbetaine, and methacryloylethyl trimethylammonium chloride and methoxy polyethylene glycol methacrylate.

I. Mechanical Foam Dispenser

The mechanical foam dispenser described herein may be selected from the group consisting of squeeze foam dispensers, pump foam dispensers, other mechanical foam dispensers, and combinations thereof. The mechanical foam dispenser may be a squeeze foam dispenser. Non-limiting examples of suitable pump dispensers include those described in WO 2004/078903, WO 2004/078901, and WO 2005/078063 and may be supplied by Albea (60 Electric Ave., Thomaston, Conn. 06787 USA) or Rieke Packaging Systems (500 West Seventh St., Auburn, Ind. 46706).

The mechanical foam dispenser may comprise a reservoir for holding the hair care composition. The reservoir may be made out of any suitable material selected from the group consisting of plastic, metal, alloy, laminate, and combinations thereof. The reservoir may be a refillable reservoir such as a pour-in or screw-on reservoir, or the reservoir may be for one-time use.

The reservoir may also be removable from the mechanical foam dispenser. Alternatively, the reservoir may be integrated with the mechanical foam dispenser. There may be two or more reservoirs.

The reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

J. Aerosol Foam Dispenser

The aerosol foam dispenser may comprise a reservoir for holding the hair care composition. The reservoir may be made out of any suitable material selected from the group consisting of plastic, metal, alloy, laminate, and combinations thereof. The reservoir may be for one-time use. The reservoir may be removable from the aerosol foam dispenser. Alternatively, the reservoir may be integrated with the aerosol foam dispenser. There may be two or more reservoirs.

The reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

K. Propellant

The hair care composition described herein may comprise from about from about 1% to about 10% propellant, alternatively from about 2% to about 8% propellant, and alternatively from about 3% to about 6% propellant, by weight of the hair care composition.

The propellant may comprise one or more volatile materials, which in a gaseous state, may carry the other components of the hair care composition in particulate or droplet form. The propellant may have a boiling point within the range of from about −45° C. to about 5° C. The propellant may be liquefied when packaged in convention aerosol containers under pressure. The rapid boiling of the propellant upon leaving the aerosol foam dispenser may aid in the atomization of the other components of the hair care composition.

Aerosol propellants which may be employed in the hair care composition may include the chemically-inert hydrocarbons such as propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene, and mixtures thereof. The propellant may comprise hydrocarbons such as isobutane, propane, and butane, and these materials may be used for their low ozone reactivity and may be used as individual components where their vapor pressures at 21.1° C. range from about 1.17 Bar to about 7.45 Bar, alternatively from about 1.17 Bar to about 4.83 Bar, and alternatively from about 2.14 Bar to about 3.79 Bar. The propellant may be hydrofluoroolefins (HFOs). The aerosol propellant can be from hydrocarbon mixtures of isobutane and propane, and can have a weight ratio of from about 85 to about 15.

L. High Melting Point Fatty Alcohol

The hair care composition is substantially free of high melting point fatty compounds. The hair compositions have less than 0.5% high melting point fatty compounds, alternatively less than 0.2%, alternatively less than 0.1% alternatively may comprise 0% high melting point fatty compounds, by weight of the hair care composition. The hair care composition may have a silicone to high melting point fatty compounds ratio of from about 100:0.

The high melting point fatty compounds have a melting point of about 25° C. or higher, and are selected from the group consisting of fatty alcohols, fatty acids, fatty alcohol derivatives, fatty acid derivatives, and mixtures thereof having a carbon chain of C10 to C30. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain carbon atoms may have a melting point of less than about 25° C. Such compounds of low melting point are not intended to be included in this section. Nonlimiting examples of the high melting point compounds are found in *International Cosmetic Ingredient Dictionary*, Fifth Edition, 1993, and *CTFA Cosmetic Ingredient Handbook*, Second Edition, 1992.

The fatty alcohols described herein are those having from about 14 to about 30 carbon atoms, alternatively from about 16 to about 22 carbon atoms. These fatty alcohols are saturated and can be straight or branched chain alcohols. Nonlimiting examples of fatty alcohols include cetyl alcohol, stearyl alcohol, behenyl alcohol, and mixtures thereof.

The fatty acids herein are those having from about 10 to about 30 carbon atoms, alternatively from about 12 to about 22 carbon atoms, and alternatively from about 16 to about 22 carbon atoms. These fatty acids are saturated and can be straight or branched chain acids. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof.

The fatty alcohol derivatives and fatty acid derivatives herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through steareth-10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e., a mixture of fatty alcohols containing predominantly cetyl and stearyl alcohol, wherein the numeric designation indicates the number of ethylene glycol moieties present; C16-C30 alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

M. Viscosity

The hair care composition may have a liquid phase viscosity of from about 1 centipoise to about 500 centipoise, alternatively from about 1 centipoise to about 450 centipoise, alternatively from about 1 centipoise to about 400 centipoise, measured at 25° C. as defined herein. The hair care composition viscosity values may be measured using a TA Instruments AR-G2 Rheometer with a concentric cylinder attachment at a shear rate of 100 reciprocal seconds at 25° C.

N. Perfume

The hair care composition may comprise from about 0.5% to about 7%, alternatively from about 1% to about 6%, and alternatively from about 2% to about 5% perfume, by weight of the hair care composition.

The hair care composition may have a silicone to perfume ratio of from about 95:5 to about 50:50, alternatively from about 90:10 to about 60:40, and alternatively from about 85:15 to about 70:30.

Examples of suitable perfumes may be provided in the CTFA (Cosmetic, Toiletry and Fragrance Association) 1992 International Buyers Guide, published by CFTA Publications and OPD 1993 Chemicals Buyers Directory 80th Annual Edition, published by Schnell Publishing Co. A plurality of perfume components may be present in the hair care composition.

O. Water Miscible Glycols

The hair care compositions described herein may comprise from about 0.1% to about 25%, alternatively from about 0.1% to about 20%, and alternatively from about 0.1% to about 15% of a water miscible glycol, by weight of the hair care composition. These water miscible glycols can improve the foam (mechanical and aerosol) stability, sustain the foam volume, thereby resulting in a foam that does not collapse during use. Non-limiting examples of suitable water miscible glycols include polyols, copolyols, alcohols, and mixtures thereof. The hair care composition may comprise from about 2% to about 20% by weight, alternatively from about 3 to about 18% by weight, alternatively from about 5% to about 15% by weight of water miscible glycols.

Examples of useful polyols include, but are not limited to, glycerin, diglycerin, propylene glycol, ethylene glycol, butylene glycol, pentylene glycol, 1,3-butylene glycol, cyclohexane dimethanol, hexane diol, polyethylene glycol (200-600), sugar alcohols such as sorbitol, manitol, lactitol and other mono- and polyhydric low molecular weight alcohols (e.g., $C_2$-$C_8$ alcohols); mono di- and oligo-saccharides such as fructose, glucose, sucrose, maltose, lactose, and high fructose corn syrup solids and ascorbic acid.

P. Optional Ingredients

The hair conditioning composition described herein may optionally comprise one or more additional components known for use in hair care or personal care products, provided that the additional components are physically and chemically compatible with the essential components described herein, or do not otherwise unduly impair product stability, aesthetics or performance. Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the conditioning composition.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, cationic polymers, viscosity modifiers, coloring agents or dyes, conditioning agents, hair bleaching agents, thickeners, moisturizers, foam boosters, additional surfactants or nonionic cosurfactants, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, non-volatile solvents or diluents (water-soluble and water-insoluble), co-solvents or other additional solvents, and similar other materials.

Method of Treating Hair

The method of treating the hair described herein comprises (1) providing a hair care composition, as described herein, (2) dispensing the hair care composition as a liquid form or a foam form using a mechanical foam dispenser or an aerosol foam dispenser; (3) applying the composition to the hair; and (4) rinsing the composition from the hair. The hair care composition can form a stable foam. A foam is stable when it substantially sustains its volume from the time of dispensing to its application on hair. The foam can have a density of from about 0.025 g/cm$^3$ to about 0.15 g/cm$^3$ when dispensed from the aerosol foam dispenser Examples The following examples illustrate the hair care composition described herein. The exemplified compositions can be prepared by conventional formulation and mixing techniques. It will be appreciated that other modifications of the present invention within the skill of those in the shampoo formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The following are non-limiting examples of the hair care composition described herein.

TABLE 1

Examples and results of rinse-off hair conditioning compositions

| Ingredient | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
|---|---|---|---|---|---|---|---|---|---|---|---|---|
| Viscosity (cps) | <50 | <50 | 1200 | 900 | <50 | <50 | <50 | <50 | <50 | <50 | Phase separation | Phase separation |
| Water | q.s. | q.s. | q.s. | q.s. | q.s. | q.s. | q.s. | q.s. | q.s. | q.s. | q.s. | q.s. |
| Cetrimonium chloride [1] | — | 1.0 | 2.5 | 2.5 | 1.0 | 1.0 | 1.0 | 1.0 | — | — | 1.0 | 1.0 |
| Behentrimonium chloride [2] | — | 1.5 | — | — | 1.5 | 1.5 | 1.5 | 1.5 | 2.5 | 2.5 | 1.5 | 1.5 |
| Distearyldimonium chloride [3] | — | 1.0 | — | — | 1.0 | 1.0 | 1.0 | 1.0 | | 1.0 | 1.0 | 1.0 |
| Aminosilicone micro-emulsion [4] | 12 | 12 | 12 | 16 | 12 | 12 | 12 | 12 | 12 | 12 | 12 | 12 |
| Cetyl alcohol [5] | — | — | 3 | 1.35 | — | — | — | — | — | — | — | — |
| Stearyl alcohol [6] | — | — | 3 | 3.15 | — | — | — | — | — | — | — | — |
| Glycerin | — | — | — | — | 10 | — | — | — | — | — | 10 | 10 |
| DPG | — | — | — | — | — | 10 | — | — | — | — | — | — |
| Guar, Hydroxylpropyl Trimonium Chloride, Jaguar C-500 [7] | — | — | — | — | — | — | — | — | — | — | 0.2 | — |
| Hydroxypropyl methylcellulose, Methocel 40-101 [8] | — | — | — | — | — | — | — | — | — | — | — | 0.2 |
| Polyox | — | — | — | — | — | — | 0.4 | — | — | — | — | — |
| PVP | — | — | — | — | — | — | — | 0.4 | — | — | — | — |
| Fragrance | 3 | 3 | 3 | 3 | 3 | 3 | 3 | 3 | 3 | 3 | 3 | 3 |
| Preservatives, pH adjusters | Up to 1% | | | | | | | | | | | |

[1] CTAC (Varisoft 100), available from Evonik
[2] BTMAC (Genamin KDMP), available from Clariant
[3] DSDMC (Varisoft TA100), available from Evonik
[4] Aminosilicone micro-emulsion (Silsoft 253), available from Momentive
[5] Cetyl alcohol, available from Procter & Gamble
[6] Stearyl alcohol, available from Procter & Gamble
[7] Jaguar C500, MW of 500,000, CD of 0.8, from Rhodia
[8] Methocel 40-101, from Dow Chemical
9. A46 (Isobutane/Propane = 84.8/15.2) available from Diversified CPC International

TABLE 2

Examples and results of aerosol foam rinse-off hair conditioning compositions

| Ingredient | Ex. 13 | Ex. 14 | Ex. 15 | Ex. 16 | Ex. 17 | Ex. 18 | Ex. 19 | Ex. 20 |
|---|---|---|---|---|---|---|---|---|
| Aerosol Foam Formation | +++ | +++ | +++ | +++ | +++ | — | +++ | +++ |
| Foam stability | + | + | +++ | +++ | +++ | — | +++ | +++ |
| Water | q.s. | q.s. | q.s. | q.s. | q.s. | q.s. | q.s. | q.s. |
| Cetrimonium chloride [1] | — | 1.0 | 2.5 | 2.5 | 1.0 | 1.0 | 1.0 | 1.0 |
| Behentrimonium chloride [2] | — | 1.5 | — | — | 1.5 | 1.5 | 1.5 | 1.5 |
| Distearyldimonium chloride [3] | — | 1.0 | — | — | 1.0 | 1.0 | 1.0 | 1.0 |
| Aminosilicone micro-emulsion [4] | 12 | 12 | 12 | 16 | 12 | 12 | 12 | 12 |
| Cetyl alcohol [5] | — | — | 3 | 1.35 | — | — | — | — |
| Stearyl alcohol [6] | — | — | 3 | 3.15 | — | — | — | — |
| Glycerin | — | — | — | — | 10 | — | 10 | 10 |
| DPG | — | — | — | — | — | 10 | — | — |
| Polyox | — | — | — | — | — | — | 0.4 | — |
| PVP | — | — | — | — | — | — | — | 0.4 |

TABLE 2-continued

Examples and results of aerosol foam rinse-off hair conditioning compositions

| Ingredient | Ex. 13 | Ex. 14 | Ex. 15 | Ex. 16 | Ex. 17 | Ex. 18 | Ex. 19 | Ex. 20 |
|---|---|---|---|---|---|---|---|---|
| Propellant [9] | 6 | 6 | 6 | 6 | 6 | 6 | 6 | 6 |
| Fragrance | 3 | 3 | 3 | 3 | 3 | 3 | 3 | 3 |
| Preservatives, pH adjusters | | | | Up to 1% | | | | |

10. CTAC (Varisoft 100), available from Evonik
11. BTMAC (Genamin KDMP), available from Clariant
12. DSDMC (Varisoft TA100), available from Evonik
13. Aminosilicone micro-emulsion (Silsoft 253), available from Momentive
14. Cetyl alcohol, available from Procter & Gamble
15. Stearyl alcohol, available from Procter & Gamble
16. Jaguar C500, MW of 500,000, CD of 0.8, from Rhodia
17. Methocel 40-101, from Dow Chemical
18. A46 (Isobutane/Propane = 84.8/15.2) available from Diversified CPC International Data Test Method A. Cone/Plate Viscosity Measurement:

The viscosities of the examples are measured by a Cone/Plate Controlled Stress Brookfield Rheometer R/S Plus, by Brookfield Engineering Laboratories, Stoughton, Mass. The cone (Spindle C-75-1) has a diameter of 75 mm and 1° angle. The viscosity is determined using a steady state flow experiment at constant shear rate of $2\ s^{-1}$ and at temperature of 26.5° C. The sample size is 2.5 ml and the total measurement reading time is 3 minutes.

B. cSt Viscosity Method

The hair care composition has a viscosity of from about 10 cSt to about 500 cSt, alternatively from about 15 cSt to about 400 cSt, alternatively from about 20 cSt to about 300 cSt, alternatively from about 25 cSt to about 250 cSt, and alternatively from about 30 cSt to about 250 cSt.

The viscosity of the hair care composition is calculated using the following method: Combine ingredients including surfactants, perfumes, viscosity reducing agents, polymers, other ingredients and the aqueous medium in a vessel. Samples are vortexed and placed into oven at 60° C. overnight to form a homogeneous solution. Samples that show hazing or clouding and formulas that appear macroscopically heterogeneous (e.g. multiple layers) at room temperature are not considered for further analysis and evaluation.

The viscosities of the formulations are measured with calibrated viscometers (Size 200/350/450) from Cannon Instrument Company (2139 High Tech Road, State College, Pa., USA, 16803). Prior to the measurement, the formulations are equilibrated in the viscometer reservoir for 30 min at 40° C. in water bath to ensure a homogeneous temperature is reached in the system.

After the equilibration, the formulations are drawn to reach the starting mark with a rubber suction bulb and the flow time between the starting mark and end mark is recorded for calculation. Each formulation is measured three times to calculate average and standard deviation. Between samples, the viscometer is cleaned with water and acetone to rinse off residual.

Viscosities are calculated based on the equation:

$$\text{Viscosity }(mm^2/s\cdot(cSt))=\text{Time }(s)*\text{Constant }(mm^2/s^2\cdot(cSt/s))$$

The time in the above equation is the flow time recorded in the experiment and the constants for each calibrated viscometer are obtained from the manuals.

C. Aerosol Foam Formation:

Aerosol foam formation is evaluated during aerosol foam dispensing. An aluminum aerosol can of 53×190 mm size from CCL Container is used.
 +++ means foam formed substantially instantly after dispensing from the aerosol can
 + means foam formed gradually after dispensing from the aerosol can
 − means no foam formed after dispensing from the aerosol can. It comes out as a liquid form.

D. Foam Stability:

Foam stability is evaluated based on the speed of the foam collapsing.
 +++ means foam substantially maintains its volume within 2 min of its formed
 + means foam starts to lose its volume after 1 min of its formed
 − means no foam formed E. Silicone Deposition Purity The method of treating hair comprises dispensing the hair care composition described herein from the aerosol foam dispenser as a dosage of foam. The foam may comprise a silicone deposition purity of from about 40% to about 100%, alternatively from about 50% to about 90%, alternatively from about 60% to about 80%, alternatively from about 50% to about 100%, alternatively from about 60% to about 100%, alternatively from about 70% to about 100%, and alternatively from about 80% to about 100%, after applying the foam to the hair and rinsing the foam from the hair.

Deposition Purity is determined by the ratio of silicone deposited per weight of hair to the total deposition of other ingredients per weight of hair. Silicone is determined by either extraction or digestion of the hair followed by an analysis with a quantitative elemental technique such as ICP for total silicon and converting to silicone based on the % of silicon in the silicone by weight. The total deposition may be determined by the sum of separate deposition measurements or by a Single Inclusive Measurement of total deposition. The separate deposition measurements may include but are not limited to: fatty alcohols, EGDS, quaternized agents and silicone. Typically these measurements involve extracting the hair then separating the ingredients of interest with chromatography and quantifying with an externally calibration based on test solution concentration. The Single Inclusive Measurement of total deposition is gravimetric. The hair is thoroughly extracted and the residue determined by weighing the dissolved residue in the extract after evaporating the solvent. This residue contains both deposited ingredients and naturally occurring extractable compounds from the hair (primarily lipids). The naturally occurring extractable compounds are quantified and subtracted from the total. These include: fatty acids, squalene, cholesterol, ceramides, wax esters, triglycerides and sterol esters. The method of quantitation is similar to the deposition measurements. Other supporting evidence of Deposition Purity may include spectroscopic or topography mapping of the hair surface.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A hair care composition suitable for mechanical and aerosol foaming comprising:
   i. from about 4% to about 20% by weight of one or more silicones, wherein the particle size of the one or more silicones is from about 1 nm to about 300 nm;
   ii. from about 0.1% to about 5% by weight of a cationic surfactant wherein the cationic surfactant has carbon chains of C20 to C40;
   iii. an aqueous carrier;
   wherein the hair care composition has a liquid phase viscosity of from about 1 centipoise to about 500 centipoise; and
   wherein the hair care composition comprises 0% fatty alcohol.

2. The hair care composition of claim 1, wherein the hair care composition further comprises from about 3% to about 20% of a nonionic emulsifier.

3. The hair care composition of claim 2, wherein the nonionic emulsifier is selected from one or more alcohol ethoxylates which are condensation products of aliphatic alcohols having from about 8 to about 18 carbon atoms, in either straight chain or branched chain configuration, and with from about 2 to about 35 moles of ethylene oxide.

4. The hair care composition of claim 1, wherein the silicone is an emulsion with a particle size of less than about 100nm.

5. The hair care composition of claim 1, having from about 0.2% to about 4% by weight of a cationic surfactant.

6. The hair care composition of claim 1, having from about 0.5% to about 3.5% by weight of a cationic surfactant.

7. The hair care composition of claim 1, having from about 0.5% to about 2.5% by weight of a cationic surfactant.

8. The hair care composition of claim 1, wherein the cationic surfactant is selected from the group consisting of behentrimonium chloride, behentrimonium methosulfate, behenamidopropyl dimethylamine, and mixtures thereof.

9. The hair care composition of claim 1, wherein the composition further comprises from about 0.2% to about 3% of di-fatty alkyl quaternary ammonium salt having a molecular structure of:

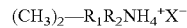

wherein $R_1$ and $R_2$ are alkyl groups with carbon chains between C12 and C20
and wherein $X^-$ is an inorganic or organic anion.

10. The hair care composition of claim 9, wherein the di-fatty alkyl quaternary ammonium salt has a molecular structure of:

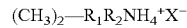

wherein $R_1$ and $R_2$ are alkyl groups with carbon chains between C14 and C18
and wherein $X^-$ is an inorganic or organic anion.

11. The hair care composition of claim 9, comprising from about 0.5% to about 2.5% by weight, of di-fatty alkyl quaternary ammonium salt.

12. The hair care composition of claim 9, wherein the di-fatty alkyl quaternary ammonium salt is selected from the group consisting of distearyldimonium chloride, dicetyldimonium chloride, and mixtures thereof.

13. The hair care composition of claim 1, wherein the composition further comprises from about 0.5% to about 5% of a mono-fatty alkyl quaternary ammonium salt having a molecular structure of

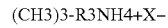

wherein R3 is alkyl groups with carbon chains between C12 and C18; and
wherein X− is an inorganic or organic anion.

14. The hair care composition of claim 13, wherein the mono-fatty alkyl quaternary ammonium salts has a molecular structure of

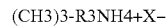

wherein R3 is alkyl groups with carbon chains between C14 and C16; and
wherein X− is an inorganic or organic anion.

15. The hair care composition of claim 13, comprising from about 0.5% to about 4% by weight of the mono-fatty alkyl quaternary ammonium salt.

16. The hair care composition of claim 13, wherein the mono-alkyl quaternary ammonium salt is cetrimonium chloride.

17. The hair care composition of claim 1, wherein the composition further comprises from about 2% to about 20% by weight of water miscible glycols.

18. The hair care composition of claim 17, wherein the composition comprises from about 5% to about 15% by weight of water miscible glycols.

19. The hair care composition of claim 17, wherein the water miscible glycols is glycerin.

20. The hair care composition of claim 1, further comprising from about 0.01% to about 0.8% by weight of a water-soluble polymer, wherein the water soluble polymer has a molecular weight of less than about 100,000 g/mol.

21. The hair care composition of claim 20, wherein the water soluble polymers are selected from the group consisting of polyethylene oxide, polyvinylpyrrolidone and mixtures thereof.

22. The hair care composition of claim 1, further comprising from about 1% to about 10% by weight of an aerosol propellant.

23. The hair care composition of claim 22, wherein the aerosol propellant is selected from hydrocarbon mixtures of butane, isobutane, propane and mixtures thereof.

24. The hair care composition of claim 23, wherein the aerosol propellant is hydrofluoroolefins.

25. The hair care composition of claim 1, wherein the hair care composition is in the form of a foam.

26. The hair care composition of claim 1, wherein the hair care composition further comprises an anti-dandruff active.

* * * * *